United States Patent
Yamamoto et al.

(10) Patent No.: US 12,195,579 B2
(45) Date of Patent: Jan. 14, 2025

(54) CELL ADHESION SHEET

(71) Applicants: FUJIFILM Corporation, Tokyo (JP); KYUSHU UNIVERSITY, NATIONAL UNIVERSITY CORPORATION, Fukuoka (JP)

(72) Inventors: Yosuke Yamamoto, Minami-ashigara (JP); Yuta Shigenoi, Minami-ashigara (JP); Atsushi Sugasaki, Minami-ashigara (JP); Masaru Tanaka, Fukuoka (JP); Shingo Kobayashi, Fukuoka (JP)

(73) Assignees: FUJIFILM Corporation, Tokyo (JP); Kyushu University, National University Corporation, Fukuoka (JP)

( * ) Notice: Subject to any disclaimer, the term of this patent is extended or adjusted under 35 U.S.C. 154(b) by 786 days.

(21) Appl. No.: 17/369,201

(22) Filed: Jul. 7, 2021

(65) Prior Publication Data
US 2021/0332180 A1 Oct. 28, 2021

Related U.S. Application Data

(63) Continuation of application No. PCT/JP2020/001969, filed on Jan. 21, 2020.

(30) Foreign Application Priority Data

Jan. 23, 2019 (JP) ................ 2019-009571
Jan. 16, 2020 (JP) ................ 2020-005258

(51) Int. Cl.
C08G 18/81 (2006.01)
C08J 5/18 (2006.01)
C12N 11/093 (2020.01)

(52) U.S. Cl.
CPC .............. *C08G 18/81* (2013.01); *C08J 5/18* (2013.01); *C12N 11/093* (2020.01)

(58) Field of Classification Search
None
See application file for complete search history.

(56) References Cited

U.S. PATENT DOCUMENTS

| | | | |
|---|---|---|---|
| 2010/0113871 A1* | 5/2010 | Dias | A61L 29/16 128/207.14 |
| 2010/0160557 A1 | 6/2010 | Murofushi et al. | |
| 2012/0052525 A1 | 3/2012 | Hay et al. | |
| 2014/0178890 A1 | 6/2014 | Kanbara et al. | |
| 2017/0335076 A1* | 11/2017 | Hatakeyama | H01B 5/16 |

FOREIGN PATENT DOCUMENTS

| | | | |
|---|---|---|---|
| JP | 2003045830 A | * | 2/2003 |
| JP | 2006-223106 A | | 8/2006 |
| JP | 2008-079598 A | | 4/2008 |
| JP | 2012-105579 A | | 6/2012 |
| JP | 2012-520667 A | | 9/2012 |
| JP | 2017-102038 A | | 6/2017 |
| WO | 2012/173097 A1 | | 12/2012 |

OTHER PUBLICATIONS

English language machine translation of JP 2003-045830 (Year: 2003).*
Dinescu et al., "Laser Processing of Organic Materials: Applications in Tissue Engineering and Chemical Sensing", Romanian Reports in Physics, vol. 65, No. 3, pp. 1019-1031, 2013 (13 pages total).
Berg et al., "Synthesis of Photopolymerizable Hydrophilic Macromers and Evaluation of Their Applicability as Reactive Resin Components for the Fabrication of Three-Dimensionally Structured Hydrogel Matrices by 2-Photon-Polymerization", Advanced Engineering Materials, 2011, vol. 13, No. 9, pp. B274-B284 (11 pages total).
International Search Report dated Mar. 24, 2020 from the International Searching Authority in International Application No. PCT/JP2020/001969.
Written Opinion dated Mar. 24, 2020 from the International Searching Authority in International Application No. PCT/JP2020/001969.
International Preliminary Report on Patentability with the translation of Written Opinion dated Jul. 27, 2021 from the International Bureau in International Application No. PCT/JP2020/001969.
Office Action dated Jun. 28, 2022 issued by the Japanese Patent office in Japanese Application No. 2020-568162.
Extended European Search Report dated Feb. 17, 2022, issued by the European Patent Office in application No. 20745734.2.

* cited by examiner

*Primary Examiner* — Megan McCulley
(74) *Attorney, Agent, or Firm* — Sughrue Mion, PLLC

(57) ABSTRACT

The present invention provides a cell adhesion sheet in which the adhesion of platelets is suppressed and the adhesion of cells is excellent. The cell adhesion sheet according to the embodiment of the present invention is formed of a composition containing a compound represented by Formula (1).

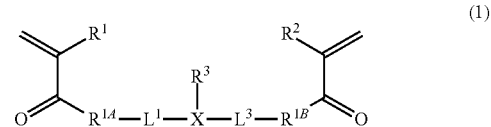

8 Claims, No Drawings

CELL ADHESION SHEET

CROSS-REFERENCE TO RELATED APPLICATIONS

This application is a Continuation of PCT International Application No. PCT/JP2020/001969 filed on Jan. 21, 2020, which claims priority under 35 U.S.C. § 119(a) to Japanese Patent Application No. 2019-009571 filed on Jan. 23, 2019 and Japanese Patent Application No. 2020-005258 filed on Jan. 16, 2020. Each of the above applications is hereby expressly incorporated by reference, in its entirety, into the present application.

BACKGROUND OF THE INVENTION

1. Field of the Invention

The present invention relates to a cell adhesion sheet.

2. Description of the Related Art

Separation/recovery technology such as a method of selectively separating/recovering target substances such as cells, bioactive substances, and proteins from body fluid such as blood, tissue fluid, and lymph, or a method of separating or removing bacteria, viruses, or the like from body tissue fluid has been used in autoimmune diseases, an acquired immunodeficiency syndrome (AIDS), prevention of acute transplant rejection, and the like.

Further, for cell medicine that detects and treats cancer cells derived from cancerous body tissues, including leukemia which is blood cancer, technology for efficiently separating or recovering cancerous cells with high sensitivity is important. In recent years, instead of a biopsy which directly collects cancer cells from cancerous tissues, a blood biopsy (liquid biopsy) which detects tumor markers or cancerous cells themselves from body tissue fluid represented by blood has been attracting attention. The conventional examination with tissue collection is a highly invasive method for a subject, whereas the blood biopsy uses a minimally invasive method such as blood collection. Therefore, it is a feature that the burden on the subject's body is extremely small. Meanwhile, in the examination using the tumor markers by the blood biopsy, site-specific tumor markers to the cancerous tissues are rarely established. For this reason, the development of technology of highly sensitively, highly efficiently, and specifically capturing and detecting the cancer cells that slightly leak into the blood from the cancerous tissues and circulate in the body (circulating cancer cells in blood) has been desired.

For example, JP2012-105579A discloses "the hydratable composition for cancer cell sorting, in which the amount of intermediate water is 30 wt % or less" (claim 4) as a hydratable composition used in a cell separation method for selectively adsorbing and separating predetermined cells existing in a living body.

SUMMARY OF THE INVENTION

Incidentally, in the cell adhesion sheet formed of the hydratable composition for cancer cell sorting disclosed in JP2012-105579A, the adhesion of platelets is suppressed, but there is room for improvement in the adhesion of cells.

An object of the present invention is to provide a cell adhesion sheet in which the adhesion of platelets is suppressed and the adhesion of cells is excellent.

As a result of diligent studies to solve the above problems, the present inventors have found that in a cell adhesion sheet formed of a composition containing a compound represented by Formula (1) described later, the adhesion of platelets is suppressed and the adhesion of cells is excellent, and have completed the present invention.

That is, the present invention is the following [1] to [8].

[1] A cell adhesion sheet which is formed of a composition containing a compound represented by Formula (1) described later.

[2] The cell adhesion sheet according to [1], in which X is a nitrogen atom.

[3] The cell adhesion sheet according to [1], in which X is $>CR^{102}-$.

[4] The cell adhesion sheet according to any one of [1] to [3], in which $R^3$ is an alkyl group.

[5] The cell adhesion sheet according to any one of [1] to [4], in which $R^3$ is an alkyl group having 4 or less carbon atoms.

[6] The cell adhesion sheet according to any one of [1] to [5], in which $R^{1A}$ and $R^{1B}$ are an oxygen atom.

[7] The cell adhesion sheet according to any one of [1] to [6], in which the compound represented by Formula (1) is selected from the group consisting of a compound represented by Formula (1-1) described later and a compound represented by Formula (1-2) described later.

[8] The cell adhesion sheet according to any one of [1] to [7], in which the cell adhesion sheet is for cancer cell adhesion.

According to the present invention, it is possible to provide a cell adhesion sheet in which the adhesion of platelets is suppressed and the adhesion of cells is excellent.

DESCRIPTION OF THE PREFERRED EMBODIMENTS

In the present specification, the range expressed by using "to" includes both values described before and after "to". For example, the range expressed by "A to B" includes A and B.

In the present specification, the solid content is intended to be a component which is contained in the composition excluding the solvent component, and the component is calculated as a solid content even in a case of liquid.

Hereinafter, the cell adhesion sheet according to the embodiment of the present invention will be described in detail.

[Cell Adhesion Sheet]

The cell adhesion sheet according to the embodiment of the present invention is a cell adhesion sheet which is formed of a composition (hereinafter, sometimes referred to as a "curable composition according to the embodiment of the present invention") containing a compound represented by Formula (1) (hereinafter, sometimes referred to as a "compound (1)") described later.

<Compound Represented by Formula (1)>

A compound represented by Formula (1) [compound (1)] will be described.

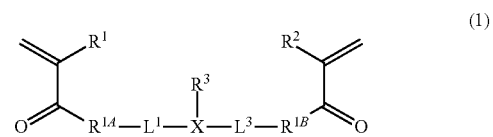

(1)

In Formula (1), the meaning of each symbol is as follows.

$R^1$ and $R^2$ each independently represent a hydrogen atom or an alkyl group, preferably a hydrogen atom or an alkyl group having 4 or less carbon atoms, more preferably a hydrogen atom, a methyl group, an ethyl group, a propyl group, or a propan-2-yl group, still more preferably a hydrogen atom or a methyl group, and even still more preferably a methyl group.

$R^3$ represents a hydrogen atom or a monovalent substituent, preferably a hydrogen atom, an alkyl group, an aryl group, or a group represented by Formula (2), more preferably a hydrogen atom, an alkyl group, a phenyl group, or a group represented by Formula (2), still more preferably an alkyl group, and even still more preferably an alkyl group having 4 or less carbon atoms. Examples of an alkyl group having 4 or less carbon atoms include a methyl group, an ethyl group, a propyl group, and a propan-2-yl group, but the present invention is not limited thereto. As an alkyl group having 4 or less carbon atoms, an ethyl group or a methyl group is preferable, and a methyl group is more preferable.

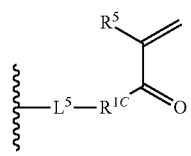

(2)

The meaning of each symbol in Formula (2) is as follows.

In Formula (2), $R^5$ represents a hydrogen atom or an alkyl group, preferably a hydrogen atom or an alkyl group having 4 or less carbon atoms, more preferably a hydrogen atom, a methyl group, an ethyl group, a propyl group, or a propan-2-yl group, and still more preferably a hydrogen atom or a methyl group.

In Formula (2), $R^{1C}$ represents an oxygen atom or —$NR^{102}$—. $R^{102}$ represents a hydrogen atom or an alkyl group, preferably a hydrogen atom or an alkyl group having 4 or less carbon atoms, more preferably a hydrogen atom, a methyl group, an ethyl group, a propyl group, or a propan-2-yl group, still more preferably a hydrogen atom or a methyl group, and even still more preferably a hydrogen atom. $R^{1C}$ is preferably an oxygen atom (—O—) or —NH—, and more preferably an oxygen atom (—O—).

In Formula (2), $L^5$ represents an aliphatic hydrocarbon group which contains a urethane bond represented by —NH—COO—*2 and which may contain an ether bond, and is preferably —$(CH_2)_m$—NH—COO—$(CH_2)_n$—, where m and n each independently are an integer of 1 to 10, preferably 2 or 3, and more preferably 2.

The urethane bond in the aliphatic hydrocarbon group represented by $L^5$ is disposed such that *2 is on the X side.

The meaning of each symbol in Formula (1) is as follows.

$R^{1A}$ and $R^{1B}$ each independently represent an oxygen atom or —$NR^{101}$—.

$R^{101}$ represents a hydrogen atom or an alkyl group, preferably a hydrogen atom or an alkyl group having 4 or less carbon atoms, more preferably a hydrogen atom, a methyl group, an ethyl group, a propyl group, or a propan-2-yl group, still more preferably a hydrogen atom or a methyl group, and even still more preferably a hydrogen atom.

$R^{1A}$ and $R^{1B}$ each independently are preferably an oxygen atom (—O—) or —NH—, and more preferably an oxygen atom (—O—).

$L^1$ and $L^3$ each independently represent an aliphatic hydrocarbon group which contains a urethane bond represented by —NH—COO—*1 and which may contain an ether bond.

$L^1$ is preferably —$(CH_2)_p$—[O—$(CH_2)_r]_t$—NH—COO—$(CH_2)_v$-*2. *2 side is bonded with X. Here, p, r, and v each independently are an integer of 1 or more, preferably an integer of 1 to 3, and more preferably 2 or 3. t is an integer of 0 or more, preferably an integer of 0 to 3, and more preferably 0 or 1.

$L^3$ is preferably *3—$(CH_2)_w$—OCO—NH—[$(CH_2)_s$—O]$_u$—$(CH_2)_q$—. *3 side is bonded with X. Here, q, s, and w each independently are an integer of 1 or more, preferably an integer of 1 to 3, and more preferably 2 or 3. u is an integer of 0 or more, preferably an integer of 0 to 3, and more preferably 0 or 1.

The urethane bond in the aliphatic hydrocarbon group represented by $L^1$ is disposed such that *2 is on the X side. Further, the urethane bond in the aliphatic hydrocarbon group represented by $L^3$ is disposed such that *1 is on the X side.

X represents a nitrogen atom or >$CR^{102}$—. Among them, from the viewpoint that difference in adhesiveness between EpCAM-negative cancer cells and EpCAM-positive cancer cells to the cell adhesion sheet easily occurs, >$CR^{102}$— is preferable.

>$CR^{102}$— is a group represented by Formula (Y). In Formula (Y), * represents a bonding position.

(Y)

In a case where X is a nitrogen atom, the compound represented by Formula (1) corresponds to a compound represented by Formula (1-1), and in a case where X is >$CR^{102}$—, the compound represented by Formula (1) corresponds to a compound represented by Formula (1-2).

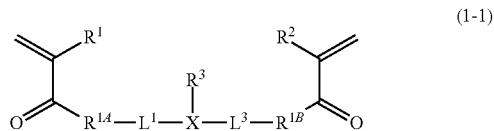

(1-1)

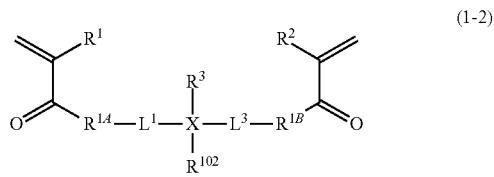

(1-2)

$R^{102}$ represents a hydrogen atom or a monovalent substituent, preferably a hydrogen atom, an alkyl group, an aryl group, or a group represented by Formula (2), more preferably a hydrogen atom, an alkyl group, a phenyl group, or a group represented by Formula (2), still more preferably an alkyl group, and even still more preferably an alkyl group having 4 or less carbon atoms. Examples of an alkyl group having 4 or less carbon atoms include a methyl group, an ethyl group, a propyl group, and a propan-2-yl group, but the present invention is not limited thereto. As an alkyl group having 4 or less carbon atoms, an ethyl group or a methyl group is preferable, and a methyl group is more preferable.

From the viewpoint of appropriately maintaining a balance between the modulus of elasticity and the flexibility of the cell adhesion sheet, the molecular weight of the compound represented by Formula (1) is preferably 200 to 1,000, more preferably 300 to 800, and still more preferably 350 to 550.

SPECIFIC EXAMPLES OF COMPOUND REPRESENTED BY FORMULA (1)

Preferred examples of the compound represented by Formula (1) include a compound represented by Formula (A), (G), (H), or (I), and among them, the compound represented by Formula (A) is particularly preferable.

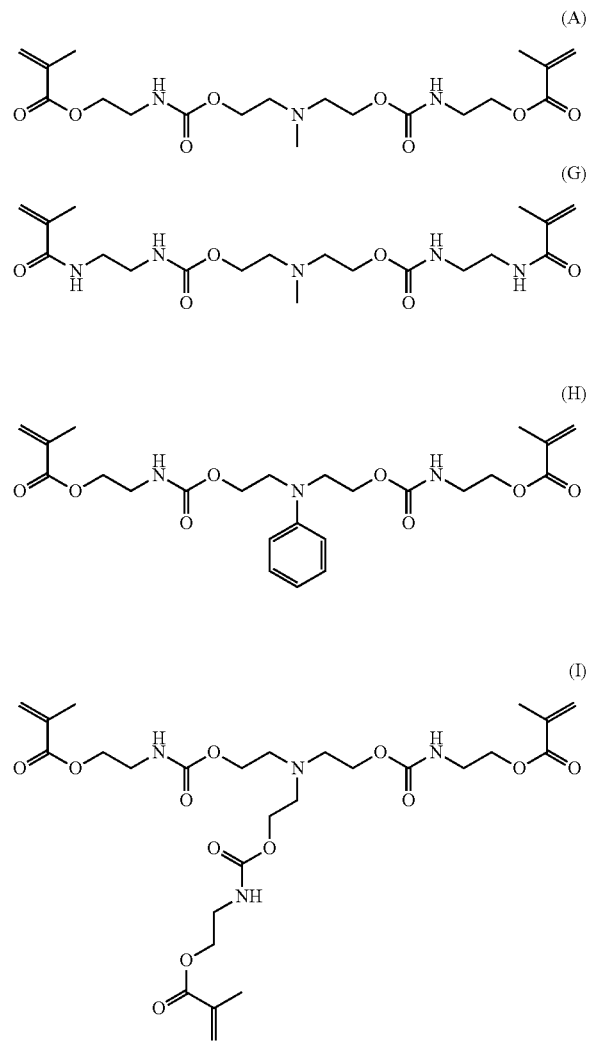

Preferred examples of the compound represented by Formula (1) include a compound represented by Formula (J) and a compound represented by Formula (K).

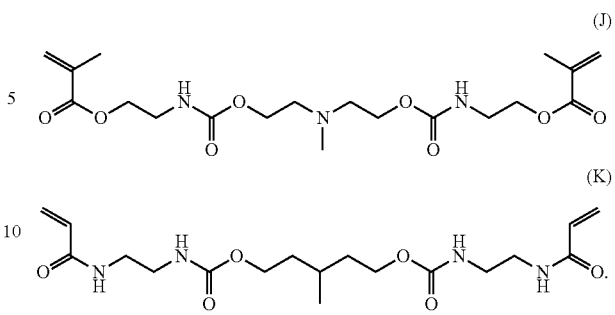

«Content of Compound Represented by Formula (1)»

The content of the compound represented by Formula (1) in the curable composition is not particularly limited, but is preferably 50% by mass or more, more preferably 75% by mass or more, still more preferably 85% by mass or more, and even still more preferably 95% by mass or more, with respect to the total mass of the solid content of the curable composition according to the embodiment of the present invention.

The upper limit of the content of the compound represented by Formula (1) in the curable composition according to the embodiment of the present invention is not particularly limited, but is usually less than 100% by mass, and preferably 99.9% by mass or less.

«Method of Synthesizing Compound Represented by Formula (1)»

The compound represented by Formula (1) can be easily synthesized by a conventionally known method.

<Components Other Than Compound (1)>

The curable composition according to the embodiment of the present invention may further contain components other than the compound (1), such as a monomer other than the compound (1), a surfactant, a polymerization initiator, a polymerization inhibitor, and a solvent, in addition to the compound (1) described above, as long as the effects of the present invention are not hindered.

«Monomer Other Than Compound (1)»

In the curable composition according to the embodiment of the present invention, a commercially available monofunctional monomer and/or polyfunctional monomer may be used in combination with the compound represented by Formula (1), in order to adjust the mechanical properties (tensile strength, abrasion resistance, or the like) of the cured film.

In a case where the curable composition according to the embodiment of the present invention contains a monomer other than the compound (1), the content of the monomer other than the compound (1) in the curable composition according to the embodiment of the present invention is not particularly limited, but is preferably more than 0% by mass and 40% by mass or less with respect to the total mass of the solid content of the curable composition according to the embodiment of the present invention. In a case where the content of the monomer other than the compound (1) is 0% by mass, which means that the curable composition according to the embodiment of the present invention does not contain any monomer other than the compound (1).

«Surfactant»

A commercially available surfactant may be added to the curable composition according to the embodiment of the present invention in order to adjust the wettability and the levelability of the curable composition to a substrate.

In a case where the curable composition according to the embodiment of the present invention contains a surfactant, the content of the surfactant in the curable composition according to the embodiment of the present invention is not particularly limited, but is preferably more than 0% by mass and 3% by mass or less with respect to the total mass of the solid content of the curable composition according to the embodiment of the present invention. In a case where the content of the surfactant is 0% by mass, which means that the curable composition according to the embodiment of the present invention does not contain the surfactant.

«Polymerization Initiator»

The polymerization initiator is not particularly limited, and examples thereof include photopolymerization initiators such as a photo-radical polymerization initiator, a photo-cationic polymerization initiator, and a photo-anionic polymerization initiator, and thermal polymerization initiators such as a thermal radical polymerization initiator and a thermal cationic polymerization initiator.

In a case where the curable composition according to the embodiment of the present invention contains a polymerization initiator, the content of the polymerization initiator in the curable composition according to the embodiment of the present invention is not particularly limited, but is preferably 0.1% by mass to 10% by mass, more preferably 0.5% by mass to 8% by mass, and still more preferably 1% by mass to 5% by mass, with respect to the total mass of the solid content of the curable composition according to the embodiment of the present invention.

«Polymerization Inhibitor»

A commercially available polymerization inhibitor may be added to the curable composition according to the embodiment of the present invention in order to impart storage stability to the compound (1) and the curable composition.

In a case where the curable composition according to the embodiment of the present invention contains a polymerization inhibitor, the content of the polymerization inhibitor in the curable composition according to the embodiment of the present invention is not particularly limited, but is preferably 0.0005% by mass to 1% by mass with respect to the total mass of the solid content of the curable composition according to the embodiment of the present invention.

«Solvent»

A solvent is not particularly limited, but is preferably alcohol, ketone, or a mixed solvent thereof, more preferably alcohol having 3 or less carbon atoms, ketone having 4 or less carbon atoms or a mixed solvent thereof, and still more preferably methanol or acetone.

In a case where the curable composition contains a solvent, the content of the solvent in the curable composition is not particularly limited, but is preferably 10% by mass to 95% by mass, and more preferably 30% by mass to 90% by mass, and still more preferably 50% by mass to 80% by mass, of the curable composition.

[Method of Producing Cell Adhesion Sheet]

The method of producing the cell adhesion sheet according to the embodiment of the present invention is not particularly limited, but examples thereof include methods described below.

<Preparation of Curable Composition>

A composition containing the compound represented by Formula (1) (hereinafter, referred to as a "curable composition") is prepared.

The curable composition may contain a polymerization initiator, a solvent, and the like, in addition to the compound represented by Formula (1).

<Formation of Curable Composition Film>

The curable composition is applied to a substrate to form a curable composition film.

The substrate is not particularly limited, but examples thereof include a glass substrate, a resin substrate, and a metal substrate.

Examples of the glass substrate include a soda-lime glass substrate, a borosilicate glass substrate, and a quartz glass substrate. The shape of the glass substrate is not particularly limited, but is preferably plate-shaped. The surface of the glass substrate may be coated or may be modified by plasma treatment or the like.

Examples of the resin substrate include a polyester-based resin substrate, a polyimide-based resin substrate, an epoxy-based resin substrate, a polyether-based resin substrate, a polysulfone-based resin substrate, and a polystyrene-based resin substrate. The shape of the resin substrate is not particularly limited, but is preferably plate-shaped or film-shaped. The surface of the resin substrate may be coated or may be modified by plasma treatment or the like.

Examples of the metal substrate include substrates made of gold, platinum, palladium, copper, manganese, silicon, molybdenum, zinc, tin, iridium, cobalt, chromium, titanium, or alloys thereof, and alumina, zirconia, hydroxyapatite, β-tricalcium phosphate (β-TCP), calcium hydrogenphosphate dihydrate, octacalcium phosphate, tetracalcium phosphate, or the like. The shape of the metal substrate is not particularly limited, but is preferably plate-shaped. The surface of the metal substrate may be coated or may be modified by plasma treatment or the like.

The method of forming the curable composition film on the substrate is not particularly limited, but examples thereof include a method using a bar coater, spin coating, dipping, painting, or the like.

<Formation of Cured Film>

The curable composition film formed on the substrate is cured to form a cured film.

The method for curing the curable composition film is not particularly limited, but it is preferable to cure the film by light irradiation or heating, and more preferable to cure the film by light irradiation. In particular, in a case where the substrate has low heat resistance, it is preferable to cure the film by light irradiation. The light irradiation may be appropriately selected from visible light rays, ultraviolet rays, electron rays, gamma rays, and the like.

The cured film which is obtained by curing the curable composition film is the cell adhesion sheet according to the embodiment of the present invention.

The cell adhesion sheet according to the embodiment of the present invention may be a sheet which is peeled off from the substrate or a sheet to which the substrate is attached. In a case of distinguishing the latter, the sheet to which the substrate is attached may be referred to as a cell adhesion sheet with a substrate.

[Cell Adhesion]

<Selectivity>

Platelets hardly adhere to the cell adhesion sheet according to the embodiment of the present invention, whereas cells easily adhere to the cell adhesion sheet. Examples of the cells include normal cells and cancer cells, and cancer cells are particularly suitable.

Examples of the normal cells include cells derived from tissues maintaining normal functions in epithelial tissues, connective tissues, muscle tissues, nerve tissues, and the like, and examples of the cancer cells include cells derived from cancerous tissues, such as breast cancer, fibrosarcoma, cervical cancer, prostate cancer, esophageal cancer, gastric cancer, colon cancer, pancreatic cancer, rectal cancer, gallbladder cancer, liver cancer, oropharyngeal cancer, lung cancer, and skin cancer.

The cell adhesion sheet according to the embodiment of the present invention has selective cell adhesion performance.

It is considered that the selective cell adhesion performance of the cell adhesion sheet according to the embodiment of the present invention may be due to intermolecular attractive force acting between a structure derived from the compound represented by Formula (1) in the cured film and a structure present on the cell surface and the protein in the serum (for example, van der Waals force defined as hydrogen bonding force, orientation force, inducing force, dispersion force, and the like), but the details are not clear.

The intermolecular attractive force can be estimated from the balance between the components constituting the surface free energy of the cell adhesion sheet, that is, the balance between the dispersion force component and the hydrogen bonding force component of the surface free energy calculated by using the Owens-Wendt equation from a contact angle of water or methylene iodide with respect to the cell adhesion sheet. The present inventors consider that the change in the balance caused by the structure of the compound according to the embodiment of the present invention leads to the change in the intermolecular attractive force, thereby exhibiting a cell adhesion selectivity.

In the surface free energy of the cell adhesion sheet, the dispersion force component is preferably 22 mNm$^{-1}$ or more, more preferably more than 25 mNm$^{-1}$ and less than 40 mNm$^{-1}$, and still more preferably 26 mNm$^{-1}$ to 38 mNm$^{-1}$. The hydrogen bonding force component is preferably 2 mNm$^{-1}$ or more, more preferably more than 5 mNm$^{-1}$ and less than 51 mNm$^{-1}$, and still more preferably 19 mNm$^{-1}$ to 45 mNm$^{-1}$.

In the present invention, the surface free energy of the cell adhesion sheet is calculated by using the Owens-Wendt equation from the result obtained by dropping a liquid droplet of pure water or methylene iodide of 1 μL to the surface using DropMaster DM-500 manufactured by Kyowa Interface Science Co., Ltd. and then measuring a contact angle after 10 seconds from the dropping.

EXAMPLES

Example 1

<Production of Cell Adhesion Sheet>

A cell adhesion sheet (hereinafter, sometimes referred to as a "sheet 1") was produced by the method described below.

1. Synthesis of Compound A

N-methyldiethanolamine (7 g, 58.7 mmol), tetrahydrofuran (100 mL), and 2-isocyanatoethyl methacrylate (19.6 g, 126 mmol) were mixed. A solution obtained by diluting Neostann U600 (377 mg; manufactured by NITTO KASEI CO., LTD.) with tetrahydrofuran (5 mL) was added dropwise to the mixed solution while paying attention to heat generation, and the solution thus obtained is stirred at a room temperature for 12 hours. The formula for the reaction is as shown below. The reaction solution was concentrated under reduced pressure and the obtained crude product was purified by being subjected to silica gel column chromatography (eluent:ethyl acetate to ethyl acetate:methanol=9:1), so that a compound represented by Formula (A) (in the present specification, referred to as a "compound A") was obtained (24 g, yield 95%). With nuclear magnetic resonance ($^1$H NMR), it was confirmed that the obtained compound was a target product.

$^1$H NMR (methanol-d$_4$, 400 MHz) δ: 1.93 (6H, s), 2.35 (3H, s), 2.71 (4H, t), 3.39 (4H, t), 4.10-4.19 (8H, m), 5.62 (2H, s), 6.12 (2H, s).

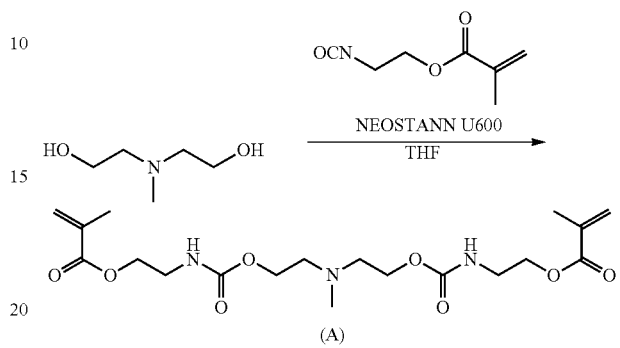

(A)

As a synthesis method of the compound A, the following conditions can also be used to carry out the same synthesis as in the method described above.

N-methyldiethanolamine (7 g, 58.7 mmol), tetrahydrofuran (100 mL), and 2-isocyanatoethyl methacrylate (19.6 g, 126 mmol) were mixed and stirred at a room temperature for 24 hours. The reaction solution was concentrated under reduced pressure and the obtained crude product was purified by being subjected to silica gel column chromatography (eluent: ethyl acetate to ethyl acetate:methanol=9:1), so that a compound represented by Formula (A) (in the present specification, referred to as a "compound A") was obtained (21 g, yield 85%).

2. Preparation of Curable Composition

The synthesized compound A (containing 30 ppm of 4-hydroxy-2,2,6,6-tetramethylpiperidine-1-oxyl (4OH-TEMPO) as a polymerization inhibitor), a polymerization initiator, and a solvent were mixed in the blending amount shown in Table 1, and a curable composition (hereinafter, referred to as a "curable composition 1") was prepared.

3. Production of Cured Film

The prepared curable composition 1 was applied onto the polyethylene terephthalate (PET) film (Cosmo shine A4300, manufactured by TOYOBO CO., LTD.; double-sided easy-adhesion treated PET film) while adjusting clearance by using a bar coater such that the thickness after drying was 3 μm, and then dried.

After that, the dried PET film was exposed at the exposure amount of 2 J/cm$^2$ by using an ultraviolet exposure machine (ECS-401G, manufactured by EYEGRAPHICS Co., Ltd.; light source was a high-pressure mercury lamp), so that a cured film was produced on the PET film.

<Evaluation of Adhesiveness>

1. Platelet Adhesiveness

A platelet adhesion experiment was conducted by using the produced cell adhesion sheet (sheet 1) and a PET film (DIAFOIL T100E125, manufactured by Mitsubishi Chemical Corporation) as a control sample. Platelet-rich plasma and platelet-poor plasma were recovered by centrifugation from human whole blood anticoagulated with sodium citrate, and platelet-rich plasma was diluted with platelet-poor plasma, thereby preparing a platelet suspension of 4×10$^7$ cells/mL. Subsequently, each sample surface came into contact with the platelet suspension at 37° C. for 60 minutes, and then was rinsed twice with a phosphate buffer solution. Then, the platelets which have adhered to each sample surface were fixed with a 1% glutaraldehyde solution. Each sample subjected to fixing treatment was washed by being immersed in a phosphate buffer solution for 10 minutes, a 1:1 mixed solution of a phosphate buffer solution and water for 8 minutes, water for 8 minutes, and water again for 8 minutes, and dried with air at a room temperature. After that, the platelets which have adhered to each sample surface of $1 \times 10^4$ µm$^2$ were observed with an electron microscope, and the number of platelets which have adhered was measured.

In a case where the total number of platelets which have adhered to the PET film (control sample) was set to 100%, the relative number of platelets in the sheet 1 was calculated, and the platelet adhesiveness was evaluated according to the following criteria.

A: 5% or less

B: more than 5% and 20% or less

C: more than 20%

2. Cancer Cell Adhesiveness 1

A cancer cell adhesion test was conducted by using, as evaluation substrates, the produced cell adhesion sheet (sheet 1) and a PET film (DIAFOIL T100E125, manufactured by Mitsubishi Chemical Corporation) as a control sample. After the surface of each substrate was washed with phosphate buffered saline, each substrate was immersed at 37° C. for 60 minutes in a 1:1 mixed medium of Dulbecco's Modified Eagle's Medium and Ham's F-12 medium (DMEM/F12 medium) prepared by adding fetal bovine serum by 10%, thereby acclimating the substrate. After this, human fibrosarcoma cells (HT-1080) suspended in the above medium were seeded into each sample at a density of $1 \times 10^4$ per 1 cm$^2$, thereby bringing the suspension and each sample into contact with each other at 37° C. for 60 minutes. Subsequently, the substrates were rinsed twice with a phosphate buffer solution, and the cells which have adhered to each substrate were fixed with a 4% paraformaldehyde solution. The cell nucleus was stained with 4',6-diamidino-2-phenylindole (DAPI) and the actin skeleton was stained with phalloidin antibody, and the number of cells which have adhered was measured using a fluorescence microscope.

In a case where the total number of cancer cells which have adhered to the PET film (control sample) was set to 100%, the relative number of cancer cells in the sheet 1 was calculated, and the cancer cell adhesiveness was evaluated according to the following criteria.

A: more than 1,500%

B: 100% or more and 1,500% or less

C: less than 100%

COMPARATIVE EXAMPLE 1

<Production of Cell Adhesion Sheet>

A compound represented by Formula (C) (sometimes referred to as a "compound C") was synthesized, and a curable composition (hereinafter, sometimes referred to as a "curable composition 2") was prepared with composition shown in Table 1.

By using the curable composition 2, a cell adhesion sheet (hereinafter, sometimes referred to as a "sheet 2") was produced in the same manner as in Example 1.

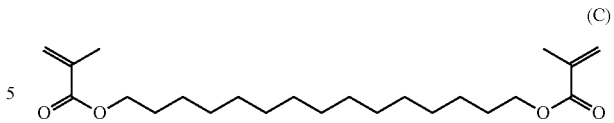

(C)

COMPARATIVE EXAMPLE 2

<Production of Cell Adhesion Sheet>

Poly(2-methoxyethyl acrylate) (20 mg) was dissolved in a solvent (methanol; 10 mL) to prepare a composition (hereinafter, sometimes referred to as a "composition 3").

By using the composition 3, a cell adhesion sheet (hereinafter, sometimes referred to as a "sheet 3") was produced in the same manner as in Example 1. As for the molecular weight of poly(2-methoxyethyl acrylate), the number average molecular weight (Mn) was 21,000 and the molecular weight distribution (Mw/Mn) was 2.8, from the results of the molecular weight analysis of GPC.

COMPARATIVE EXAMPLE 3

A PET film (DIAFOIL T100E125, manufactured by Mitsubishi Chemical Corporation) was used as a cell adhesion sheet (hereinafter, sometimes referred to as a "sheet 4").

TABLE 1

| | | Example 1 | Comparative Example 1 |
|---|---|---|---|
| Compound | Compound A | 19.40 | |
| | Compound C | | 19.63 |
| Polymerization initiator | PI-1 | 0.60 | |
| | Irg1173 | | 0.37 |
| Solvent | Methanol | 90.00 | |
| | Acetone | | 80.00 |
| Total | | 100.00 | 100.00 |
| | | | Parts by mass |

In Table 1, PI-1 in the column of polymerization initiator represents a photopolymerization initiator (a compound represented by the following formula), and Irg1173 represents a photopolymerization initiator (Omnirad 1173, manufactured by IGM Resins).

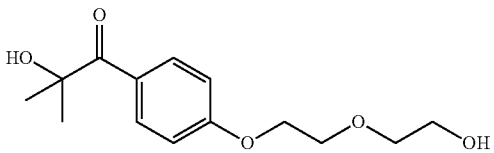 [SMILES: CC(C)(O)C(=O)c1ccc(OCCOCCO)cc1]

As PI-1, a compound obtained by synthesis with reference to the method described in paragraphs [0105] to [0110] of WO2017/018146A was used.

By using the cell adhesion sheets of Comparative Examples 1 to 3, platelet adhesiveness and cancer cell adhesiveness 1 were evaluated in the same manner as in Example 1. The evaluation results are shown in Table 2.

TABLE 2

|  | Example | Comparative Example | | |
|---|---|---|---|---|
|  | 1 | 1 | 2 | 3 |
|  | Sheet | | | |
|  | 1 | 2 | 3 | 4 |
| Platelet adhesiveness | A | B | A | C |
| Cancer cell adhesiveness 1 | A | C | B | B |

In the cell adhesion sheet of Example 1, the number of platelets which have adhered was small and the number of cancer cells which have adhered was large.

Further, as a result of evaluating the adhesiveness regarding other cancer cells (SW480, HT29, MCF-7, A549, HeLa, and MDA-MB-231) by using the sheet 1 of Example 1, it was confirmed that the cancer cells had the same cell adhesiveness as that of HT1080. On the other hand, as a result of evaluating the adhesiveness regarding normal human dermal fibroblasts (NHDF), which are epithelial tissues of normal cells, it was confirmed that the number of the fibroblasts which have adhered was smaller than that of cancer cells.

Example 2

<Production of Cell Adhesion Sheet>

With reference to the synthesis of the compound A, a compound represented by Formula (B) (sometimes referred to as a "compound B") was synthesized, and a curable composition (hereinafter, sometimes referred to as a "curable composition 4") was prepared with composition shown in Table 3.

By using the curable composition 4, a cell adhesion sheet (hereinafter, sometimes referred to as a "sheet 5") was produced in the same manner as in Example 1.

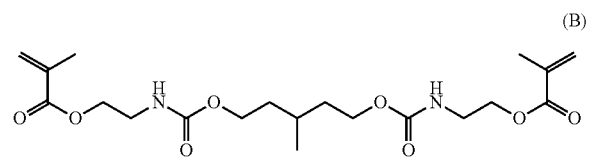 [SMILES: C=C(C)C(=O)OCCNC(=O)OCCC(C)CCOC(=O)NCCOC(=O)C(=C)C]

(B)

TABLE 3

|  |  | Example 2 |
|---|---|---|
| Compound | Compound B | 19.63 |
| Polymerization initiator | Irg1173 | 0.37 |
| Solvent | Acetone | 80.00 |
| Total |  | 100.00 Parts by mass |

By using the produced cell adhesion sheet (sheet 5), the platelet adhesiveness evaluation and the following evaluation (3. Cancer Cell Adhesiveness 2) were conducted in the same manner as in Example 1. The evaluation results are shown in Table 4.

3. Cancer Cell Adhesiveness 2

A cancer cell adhesion test was conducted by using, as evaluation substrates, the produced cell adhesion sheet (sheet 5) and a PET film (DIAFOIL T100E125, manufactured by Mitsubishi Chemical Corporation) as a control sample. After the surface of each substrate was washed with phosphate buffered saline, each substrate was immersed at 37° C. for 60 minutes in a 1:1 mixed medium of Dulbecco's Modified Eagle's Medium and Ham's F-12 medium (DMEM/F12 medium) prepared by adding fetal bovine serum by 10%, thereby acclimating the substrate. After that, MDA-MB-231 (human-derived invasive malignant breast cancer cell line) suspended in the above medium was seeded into each sample at a density of $1\times10^4$ per 1 $cm^2$, thereby bringing the suspension and each sample into contact with each other at 37° C. for 60 minutes. Subsequently, the substrates were rinsed twice with a phosphate buffer solution, and the cells which have adhered to each substrate were fixed with a 4% paraformaldehyde solution. The cell nucleus was stained with 4',6-diamidino-2-phenylindole (DAPI) and the actin skeleton was stained with phalloidin antibody, and the number of cells which have adhered was measured using a fluorescence microscope.

In a case where the total number of cancer cells which have adhered to the PET film (control sample) was set to 100%, the relative number of cancer cells in the sheet 5 was calculated, and the cancer cell adhesiveness was evaluated according to the following criteria.

A: more than 1,500%
B: 100% or more and 1,500% or less
C: less than 100%

TABLE 4

|  | Example 2 |
|---|---|
|  | Sheet 5 |
| Platelet adhesiveness | A |
| Cancer cell adhesiveness 2 | A |

In the cell adhesion sheet 5 of Example 2, the number of platelets which have adhered was small and the number of cancer cells which have adhered was large.

<Evaluation of Adhesion Selectivity>

After MDA-MB-231 (human-derived invasive malignant breast cancer cell line) and MCF-7 (human-derived benign tumor cell line) each were cultured in a 1:1 mixed medium of Dulbecco's Modified Eagle's Medium and Ham's F-12 medium (DMEM/F12 medium) prepared by adding fetal bovine serum by 10%, MDA-MB-231 cells were stained with CellTracker Red CMTPX, and MCF-7 cells were stained with CellTracker Green CMFDA. Each group of cells was mixed into the DMEM/F12 medium at a density of $0.5\times10^4$ per 1 $cm^2$ (total $1\times10^4$ per 1 $cm^2$), and the respective mixtures were seeded into the sheets 1 and 5, thereby bringing the respective mixtures into contact with the sheets 1 and 5 at 37° C. for 60 minutes.

Subsequently, the sheets 1 and 5 were rinsed with a phosphate buffer solution, and cells which have adhered to each of the sheets 1 and 5 were fixed with a 4% paraformaldehyde solution. The sheets 1 and 5 after cell fixing were rinsed with a phosphate buffer solution, and then were sealed on the slide glass by using Prolong gold antifade mountant with DAPI. Then, the number of cells which have adhered to each sheet was measured by using a fluorescence microscope.

Both the numbers of MDA-MB-231 (human-derived invasive malignant breast cancer cell line) cells which have adhered onto the sheets 1 and 5, respectively, and the numbers of MCF-7 (human-derived benign tumor cell line)

cells which have adhered onto the sheets 1 and 5, respectively, were measured, and the cell adhesion selectivity was evaluated according to the following criteria.

A: The ratio of (the number of MDA-MB-231 cells which have adhered to the number of MCF-7 cells which have adhered) is 2 or more.

B: The ratio of (the number of MDA-MB-231 cells which have adhered to the number of MCF-7 cells which have adhered) is less than 2.

The sheet 1 was evaluated as "B" and the sheet 5 was evaluated as "A".

From the above results, it was confirmed that the cell adhesion sheet (sheet 5) formed of a composition containing a compound represented by Formula (1-2) rather than the cell adhesion sheet (sheet 1) formed of a composition containing a compound represented by Formula (1-1) had the cell adhesion selectivity. The conventional cell adhesion sheets had no adhesion selectivity between EpCAM-negative cancer cells (MDA-MB-231) and EpCAM-positive cancer cells (MCF-7), but surprisingly, it was confirmed that the sheet 5 had the adhesion selectivity between both the cells.

What is claimed is:

1. A cell adhesion sheet which is formed of a composition containing a compound represented by Formula (1),

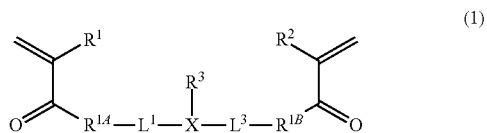

(1)

in Formula (1), $R^1$ and $R^2$ each independently represent a hydrogen atom or an alkyl group, $R^3$ represents a hydrogen atom or a monovalent substituent, $R^{1A}$ and $R^{1B}$ each independently represent an oxygen atom or $-NR^{101}-$, where $R^{101}$ represents a hydrogen atom or an alkyl group, $L^1$ and $L^3$ each independently represent an aliphatic hydrocarbon group which contains a urethane bond represented by $-NH-COO-*1$ and which may contain an ether bond, and X represents a nitrogen atom, and the urethane bond in the aliphatic hydrocarbon group represented by $L^1$ is disposed such that *1 is on an X side, and the urethane bond in the aliphatic hydrocarbon group represented by $L^3$ is disposed such that *1 is on the X side.

2. The cell adhesion sheet according to claim 1, wherein $R^3$ is an alkyl group.

3. The cell adhesion sheet according to claim 2, wherein $R^3$ is an alkyl group having 4 or less carbon atoms.

4. The cell adhesion sheet according to claim 2, wherein $R^{1A}$ and $R^{1B}$ are an oxygen atom.

5. The cell adhesion sheet according to claim 1, wherein $R^3$ is an alkyl group having 4 or less carbon atoms.

6. The cell adhesion sheet according to claim 1, wherein $R^{1A}$ and $R^{1B}$ are an oxygen atom.

7. The cell adhesion sheet according to claim 1, wherein the compound represented by Formula (1) is selected from the group consisting of a compound represented by Formula (A)

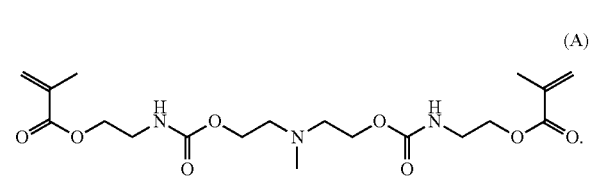 [SMILES: C=C(C)C(=O)OCCNC(=O)OCCN(C)CCOC(=O)NCCOC(=O)C(=C)C]

(A)

8. The cell adhesion sheet according to claim 1, wherein the cell adhesion sheet is for cancer cell adhesion.

* * * * *